United States Patent [19]

Duinker et al.

[11] 4,313,941

[45] Feb. 2, 1982

[54] STABILIZED GRANULAR NEMATICIDAL AND INSECTICIDAL COMPOSITION HAVING O-ETHYL-S,S-DIPROPYL DITHIOPHOSPHATE AS AN ACTIVE SUBSTANCE

[75] Inventors: Hendrik Duinker; Willem de Lange, both of Weesp, Netherlands

[73] Assignee: Duphar International Research B.V., Netherlands

[21] Appl. No.: 137,350

[22] Filed: Apr. 7, 1980

Related U.S. Application Data

[63] Continuation of Ser. No. 10,272, Feb. 7, 1979, abandoned.

[30] Foreign Application Priority Data

Feb. 9, 1978 [NL] Netherlands ........................ 7801475

[51] Int. Cl.$^3$ ...................... A01N 57/40; C07F 9/165

[52] U.S. Cl. .................................... 424/225; 260/989
[58] Field of Search ........................ 260/989; 424/225

[56] References Cited

U.S. PATENT DOCUMENTS 3,112,244 11/1963 Goyette ............................. 424/225
3,268,393 8/1966 Wilson, Jr. ......................... 424/225

FOREIGN PATENT DOCUMENTS 1147936 4/1969 United Kingdom .

*Primary Examiner*—Anton H. Sutto
*Attorney, Agent, or Firm*—Stevens, Davis, Miller & Mosher

[57] ABSTRACT

The invention relates to a stabilized granular nematicidal and insecticidal composition having O-ethyl-S,S-dipropyl dithiophosphate as an active substance which contains pumice granules as a stabilizing carrier.

8 Claims, No Drawings

STABILIZED GRANULAR NEMATICIDAL AND INSECTICIDAL COMPOSITION HAVING O-ETHYL-S,S-DIPROPYL DITHIOPHOSPHATE AS AN ACTIVE SUBSTANCE

This is a continuation, of application Ser. No. 010,272, filed Feb. 7, 1979 now abandoned.

The invention relates to a stabilized granular nematicidal and insecticidal composition having O-ethyl-S,S-dipropyl dithiophosphate as an active substance, as well as to a method of preparing said composition, and to a method of preventing or controlling nematodes and soilborne insects.

It is known from U.S. Pat. Nos. 3,112,244 and 3,268,393 that O-ethyl-S,S-dipropyl dithiophosphate can be used against nematodes and soilborne insects in agriculture and horticulture. In order to effect a uniform distribution of the active substance over an acreage of lead under treatment, a carrier is usually used. As solid carrier materials are mentioned sand and clay, for example, several types of clay such as kaolinite, bentonite and attapulgite.

O-ethyl-S,S-dipropyl dithiophosphate is marketed as a granular composition under the tradename MOCAP 10 G (registered trademark), in which the active substance is carried on clay, namely attapulgite or montmorillonite. It is generally known that such kinds of clay can accelerate the decomposition of the active substance so that for a composition in which clay is employed as a carrier a stabilizer, for example, a glycol or glycol ether, is necessary. It has consequently been found that the above-mentioned commercial product contains approximately 5% of propylene-glycol to improve the storage stability.

Furthermore, the soil is usually treated against nematodes and noxious insects living in the soil in a given season, namely in the spring prior to the sowing or planting. In the case of a regular production of the composition it may therefore occur that the finished composition has to be stored for nearly a year before it is used, often under very varying circumstances of temperature and air humidity. Frequently a good storage stability of even two years is demanded because a part of the stored stock may remain unused by the user for one year. Therefore the storage stability is of great importance. Although the addition of a glycol to the above-mentioned formulation improves the storage stability, such an addition is a disadvantage both from cost and environmental considerations. As a matter of fact, such an addition causes an increase of the cost of the finished product and moreover, when used in the soil, it pollutes the environment.

It has now been found that these disadvantages can be removed by using pumice granules in the composition as a stabilizing carrier for the active substance.

The storage stability of said formulation with O-ethyl-S,S-dipropyl dithiophosphate as an active substance and pumice granules as a carrier is excellent. The storage stability proves to be even better than that of a known formulation on clay to which propylene glycol has been added. As will become apparent from the example, a composition on the basis of pumice to which in addition a glycol has been added, has a significantly worse stability than a composition without such an addition, so that the addition of a "stabilizer" is not only superfluous but is even undesirable. The activity of the active substance is not detrimentally influenced; a composition according to the invention shows a strong nematicidal activity.

An additional advantage of the composition according to the invention is that the product is considerably less dusty than the known formulation on clay. This is an important advantage both in packaging the product and for the user when strewing on the soil; O-ethyl-S,S-dipropyl dithiophosphate must as a matter of fact be considered as a poisonous substance with which any contact should be avoided as much as possible.

Finally, it has been found that the active substance can be provided on pumice granules more simply than on clay granules. In the former case, commonly employed mixing apparatuses, for example a Nauta mixer, may be used, whereas the formulation on clay granules should be carried out in an impregnating apparatus which is suitable for this purpose so as to obtain a granular composition of a satisfactory quality.

Pumice granules of a technical quality may be used for the compositions according to the invention. It is known that the quality and hence the absorbing power of technical pumice may vary considerably. In order to achieve a desired concentration of active substance in the composition a filler may be used which results in a cost-price technical advantage. Sand and marble grit have proved to give particularly good satisfaction as inert granular fillers. With these granular fillers, the content of active substance in the composition can be adjusted at the desired value irrespective of the absorbing power of the pumice quality used. This desired concentration of active substance in the composition may vary between 2 and 30% by weight. A composition is preferably used which contains from 9 to 22% by weight of active substance. When a composition with such a content of a active substance is used, a distribution of the active substance which is as uniform as possible over the soil surface to be treated is obtained. The dosage of a composition according to the invention desired for application will depend inter alia on the type of nematodes or soil-borne insects which are to be controlled and the type of soil. In general it holds that favourable results are obtained with a dosage which corresponds to 3 to 50 kg of the active substance per hectare.

The invention will now be described in greater detail with reference to the following specific examples.

EXAMPLE 1

71.7% by weight of pumice granules and 6.0% by weight of sand were mixed in a Nauta mixer, after which 21.3% by weight of O-ethyl-S,S-dipropyl dithiophosphate (94%) were added. When the active substance is distributed homogeneously over the carrier material, the resulting composition was dyed with 1.0% by weight of ultramarine blue. The final product is a blue-coloured granular composition.

An approximately 10% composition was obtained in a corresponding manner by impregnating 10.65% by weight (94%) O-ethyl-S,S-dipropyl dithiophosphate on a mixture of 63.35% by weight of pumice granules and 25.0% by weight of sand; dying with 1.0% by weight of ultramarine blue.

EXAMPLE 2

The storage stability of granular compositions having O-ethyl-S,S-dipropyl dithiophosphate as an active substance on various solid inert carriers at 54° C. is shown in the following Table.

| Carrier | Stabilizer | Content[2] of active substance after.....months | | | | | |
|---|---|---|---|---|---|---|---|
| | | 0 | 1 | 3 | 5 | 6 | 11 |
| pumice; origin A | none | 9.6 | | | | | 9.8 |
| pumice; origin A | 5% propylene-glycol | 10.4 | | | 8.6 | | |
| pumice; origin B | none | 11.0 | 10.6 | | 10.1 | | |
| pumice; origin C | none | 10.5 | | | 9.9 | | |
| MOCAP 16 (trade-mark) | | 9.4 | | 7.7 | | 4.6 | |
| attapulgite | none | 8.6 | 7.3 | | 5.2 | | |
| attapulgite | 5% propylene-glycol | 9.8 | 9.5 | | 7.6 | | |
| Smecta a 450[1] (trade-mark) | none | 9.1 | | 6.55 | | | |
| Smecta A450 | 5% propylene-glycol | 10.1 | | 8.5 | | | |

Remarks:
[1] Smecta A450 is a European type of clay of the type attapulgite or montmorillonite.
[2] The content of active substance was determined by means of a gas chromotographic analysis method.

From the above table it appears that the three formulations containing pumice of different origins are considerably more stable in storage than the composition having clay as a carrier, even when propylene glycol as a stabilizer is added to the latter compositions. It also appears that propylene glycol has an adverse influence on the stability of a composition on the basis of pumice.

EXAMPLE 3

The nematicidal activity of a formulation of the invention having O-ethyl-S,S-dipropyl dithiophosphate as an active substance in a concentration of approximately 10% was determined in the following manner.

A granular composition having O-ethyl-S,S,-dipropyl dithiophosphate as an active substance was strewed on plots of horticultural soil of approximately 70 m² in two places, namely in Boskoop, Netherlands, on peat soil, and in Zundert, Netherlands on sandy soil. The soil treatment in Boskoop took place on Apr. 7, that in Zundert on March 7. The compositions were worked into the soil approximately 25 cm deep. Young plants were then planted in the soil, in Boskoop on approximately April 15, in Zundert on May 8. The crop consisted of a mixture of the following plants: Skimmia, Ligustrum, Rhododendron, Chamaecyparis, Cotoneaster, Thuya occidentalis, Acacia, Taxus, Berberis, Cyperus and Betula. The nematicidal activity of the compositions was determined by taking soil samples immediately after the treatment and after approximately 6 months and determining the degree of infestation thereof. Said degree of infestation was determined by counting the number of free-living eelworms in the soil samples. The eelworms Tylenchidae and Saprophage present in the soil were counted. The ratio between the population value at the end with respect to that at the beginning of the test is termed the increase factor (increase f.). For comparison, the degree of infestation of the untreated soil was determined.

The following results were obtained:

| granular carrier | dosage in kg of comp. per hectare | test in Boskoop number of free-living eelworms per 100 ml of soil | | |
|---|---|---|---|---|
| | | 7-4 | 15-10 | increase. f. |
| untreated | — | 2610 | 1280 | 0.5 |
| pumice | 200 | 3620 | 170 | 0.05 |

| granular carrier | dosage in kg of comp. per hectare | test in Zundert number of free-living eelworms per 100 ml of soil | | |
|---|---|---|---|---|
| | | 7-3 | 15-10 | increase. f. |
| untreated | — | 2300 | 2640 | 1.2 |
| pumice | 200 | 2340 | 1100 | 0.5 |

From this example it appears that a composition having O-ethyl-S,S,-dipropyl dithiophosphate as an active substance and pumice granules as a carrier material shows a strong nematicidal activity.

What is claimed is:

1. A stabilized granular nematicidal and insecticidal composition comprising O-ethyl-S,S,-dipropyl dithiophosphate, in an nematicidally and/or insecticidally effective amount and, as a carrier and as essentially the sole stabilizer, pumice granules in an amount sufficient to stabilize said composition.

2. A method for the control of nematodes and soilborne insects comprising contacting said soil with a composition of claim 1 in amounts such that each hectare is contacted with from 3 to 50 kilograms of the dithiophosphate.

3. A composition as claimed in claim 1, characterized in that the inert filler is sand or marble grit.

4. The composition of claim 1 wherein in addition an inert granular filler is present.

5. The composition of claim 1 wherein the dithiophosphate is present in the concentration of from 2 to 30% by weight.

6. The composition of claim 4 wherein the dithiophosphate is present in the concentration of from 2 to 30% by weight.

7. The composition of claim 5 wherein the dithiophosphate is present in the concentration of from 9 to 22% by weight.

8. The composition of claim 6 wherein the dithiophosphate is present in the concentration of from 9 to 22% by weight.

* * * * *